United States Patent [19]
Lancel

[11] Patent Number: 5,929,065
[45] Date of Patent: *Jul. 27, 1999

[54] METHOD FOR TREATING SLEEP DISORDERS

[75] Inventor: Marike Lancel, Munich, Germany

[73] Assignee: Max-Planck-Gesellschaft zur Forderung der Wissenschaften e.V., Berlin, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/609,461

[22] Filed: Mar. 1, 1996

[30] Foreign Application Priority Data

Jul. 13, 1995 [DE] Germany .................. 195 25 598

[51] Int. Cl.$^6$ .................................................. A01N 55/02
[52] U.S. Cl. ............................................................ 514/188
[58] Field of Search ................................................ 514/188

[56] References Cited

U.S. PATENT DOCUMENTS

| | | | |
|---|---|---|---|
| 4,362,731 | 12/1982 | Hill | 424/256 |
| 4,786,647 | 11/1988 | Simpkins et al. | 514/355 |
| 5,167,228 | 12/1992 | Czeisler et al. | 128/395 |
| 5,354,760 | 10/1994 | Petersen et al. | 514/326 |

OTHER PUBLICATIONS

Tominaga et al., "GABA A receptor agonist muscimol can reset the phase of neural activity rhythm in the rat suprachiasmatic nucleus in vitro", Neuroscience Letters, 166:81–84, 1994.

LLoyd et al., "The potential use of GABA agonists in psychiatric disorders: evidence from studies with progabide in animal models and clinical trials", Pharamacology Biochemistry and Behavior, 18:957–966, 1983.

de Bittencourt et al., "Vigabatrin: clinical evidence supporting rational polytherapy in management of uncontrolled seizures", Epilepsia, 35(2):373–380, 1994.

Camacho–Arroyo et al., Neuroscience Letters; 129(1):95–97, Aug. 5, 1991.

LLoyd et al., Pharmacology Biochemistry & Behavior, 18:957–966, 1983.

Chweh, A.Y. et al. (1987) "Hynoptic Action Of Pentobarbital In Mice: A Possible Mechanism," *Expt. Neurology* 97:70–76.

Depaulis, A. et al. (1988) "Evidence That Activation Of GABA Receptors In the Substantia Nigra Suppresses Spontaneous Spike–And–Wave Discharge In The Rat," *Brain Research* 448:20–29.

Fariello, R.G. et al. (1984) "Metabolic Correlates Of GABAmimetic–Induced EEG Abnormalities," in *Neurotransmitter. Seizures and Epilepsy*, R.G. Fariello et al., eds, Raven Press, New York, pp. 245–252.

Lancel, M. And Faulhaber, J. (1996) "The GABA$_A$ Agonist THIP (gaboxadol) Increases Non–REM Sleep And Enhances Delta Activity In The Rat," *NeuroReport* 7:2241–2245.

*Primary Examiner*—Donna C. Wortman
*Assistant Examiner*—Brenda G. Brumback
*Attorney, Agent, or Firm*—John P. White; Cooper & Dunham LLP

[57] ABSTRACT

The invention relates to a method of treating sleep disorders in a patient in need thereof comprising the administration of a hypnotically effective amount of a non-allosteric GABA$_A$ agonist.

10 Claims, No Drawings

METHOD FOR TREATING SLEEP DISORDERS

FIELD OF THE INVENTION

This invention relates to a method of treating sleep disorders comprising the administration of non-allosteric $GABA_A$ agonists.

BACKGROUND

The hypnotics most frequently prescribed for the treatment of sleep disorders are classic benzodiazepines as well as compounds like zolpidem and zopiclone. These compounds shorten sleep latency and increase total sleep time. The pharmacological effect of these compounds is assumed to be due to a modulation of the $GABA_A$ receptor ($\gamma$-aminobutyric-acid$_A$ receptor); however they neither increase neuronal release of GABA nor block the reuptake of released GABA. They have no direct $GABA_A$ agonistic effect either. On the contrary, they react with specific binding sites which belong to a complex consisting of GABA receptors, various distinct modulatory receptors among others for benzodiazepines and a chlorine ion channel, and thus cause the $GABA_A$ receptor to undergo an allosteric change. This allosteric change influences the efficacy of GABA in promoting chloride channel opening.

However, such $GABA_A$ receptor modulators exhibit considerable side effects. Especially with the use of benzodiazepines, tolerance and dependency develop rapidly, and rebound insomnia, which will manifest itself by restlessness and somnipathy, emerges upon withdrawal.

Furthermore, the quality of sleep induced by said $GABA_A$ receptor modulators is unphysiological. REMS (=rapid eye movement sleep) as well as the deeper phases of nonREMS (slow-wave sleep) are disturbed.

For example, benzodiazepines and all other common hypnotics cause the following sleep profile.
1) they inhibit REMS
2) they promote nonREMS
3) they decrease delta activity (0.5–4 Hz) in the EEG within nonREMS by
   a) reducing the rate of rise of delta activity at the beginning the nonREMS episodes, and
   b) reducing the maximum delta activity during nonREMS episodes.

In one of two studies, Mendelson et al. (Life Sci 47, (1990) PL 99, 101; Life Sci 53 (1993) PL 81–87) found that muscimol, a GABA analogue and selective $GABA_A$ agonist, does cause a slight reduction of sleep latency but does not influence sleep as such. This finding resulted in the common opinion that non-benzodiazepoid $GABA_A$ agonists are devoid of any clinical beneficial effects on sleep disorders. Furthermore, it is generally accepted in the field that if a substance has a sedative side effect or causes a slight reduction in sleep latency, this will not justify its classification as a hypnotic.

In Pharmacol. Biochem. and Behaviour (1993), vol 45, 881–887, Suzuki et al investigated the effect of 3 mg/kg muscimol IP in different inbred strains of rats (Fischer 344, and Lewis) by measuring the loss and duration of the righting reflex. The authors of this document equate the duration of loss of the righting reflex to an hypnotic effect (sleep time). However, it is well established that the bahavioral parameter "righting reflex" bears no relationship with sleep. In the rat, very high doses of muscimol, such as 3 mg/kg, are known to evoke absence epilepsy. It is in fact highly likely tht the perceived sedation ("loss of righting reflex") represents a pathological state of an epileptiform nature (see "Hypersynchronisation and Sedation Produced by GABA-Transaminase Inhibitors and picrotoxin: Does GABA Participate in Sleep Control?", Waking and Sleeping (1979), 3: 245–254).

In U.S. Pat. No. 5,185,446 cycloalkylinidazo pyrimidine derivatives are disclosed which are described as being selective agonists, antagonists or inverse agonists for $GABA_A$ brain receptors and may be used in the diagnosis and treatment of anxiety, sleep and other disorders. All of these compounds are, however, allosteric $GABA_A$-receptor modulators. In Pharmacol. Biochem. and Behaviour (1988), vol 29, 781–783, the hypnotic affects of the allosteric $GABA_A$-receptor modulators are described.

The object underlying the present invention is to provide an effective hypnotic which has no significant side effects and causes a sleep profile essentially corresponding to physiological sleep.

SUMMARY OF THE INVENTION

The present invention provides a method of treating sleep disorders in a patient in need thereof comprising the administration of a hypnotically effective amount of a non-allosteric $GABA_A$ agonist.

DETAILED DESCRIPTION OF THE INVENTION

The present invention is based on the unexpected finding that the $GABA_A$ agonists muscimol and THIP (4,5,6,7-tetrahydroisoxazolo(5,4-C)pyridin-3-ol) have very advantageous effects on sleep. The activity profiles of muscimol- and THIP-induced sleep can be summarized as follows:
1) The total duration of nonREMS and REMS is increased after muscimol and THIP increases nonREMS, without decreasing REMS.
2) Prolongation of nonREMS episodes as well as REMS episodes, which reflects an increase in sleep maintenance.
3) The EEG-delta activity within nonREMS is enhanced; this is achieved by
   a) increasing the rise rate of delta activity at the beginning of each nonREMS episode,
   b) increasing the maximum delta activity during the nonREMS episodes, and
   c) prolonging the nonREMS episodes (see 2).

All above-summarized changes correspond to the sleep profile observed with a physiological increase in sleep need, for instance, after an extended period of wakefulness. This shows that a non-allosteric $GABA_A$ agonist, unlike benzodiadepines and all other common hypnotics, can induce sleep having the characteristics of natural sleep.

Results similar to those observed using the full $GABA_A$ agonist muscimol and the partial $GABA_A$ agonist THIP could also be achieved by using other non-allosteric $GABA_A$ agonists, GABA transaminase inhibitors, such as vigabatrin, and GABA uptake inhibitors, such as tiagabine. It was thus found that the pharmacological stimulation of the GABA binding site of the $GABA_A$ receptor, either directly by administering a $GABA_A$ agonist or indirectly by increasing the endogenous GABA concentration by way of a GABA prodrug, GABA uptake inhibitor or GABA transaminase inhibitor, can be of considerable therapeutic advantage in the treatment of sleep disorders.

Thus, the invention relates to a method of treating sleep disorders in a patient in need thereof comprising the administration of a substance which either directly or indirectly stimulates GABA binding sites of the $GABA_A$ receptor in an hypnotically effective amount. Substances which stimulate the GABA binding site of $GABA_A$ receptors are referred to herein as non-allosteric $GABA_A$ agonists.

Examples of such compounds include in particular:
$GABA_A$ agonists which exert a direct effect on $GABA_A$ receptors, such as muscimol, thiomuscimol, THIP, thioTHIP, isoguvacine,
GABA prodrugs, such as progabide,
GABA uptake inhibitors, such as tiagabine and
GABA transaminase inhibitors, such as vigabatrin.

Especially preferred is the use of partial agonists since they do not result in a rapid desensitisation of the $GABA_A$ receptor.

Due to their pharmacological properties, the above-mentioned substances having a direct or indirect non-allosteric agonistic effect on the $GABA_A$ receptor are therapeutically beneficial in a broad range of sleep disorders, including difficulties in falling asleep, frequent nocturnal arousals, early morning awakening and/or a dissatisfaction with the intensity of sleep.

The compounds are particularly suitable for the treatment of elderly patients.

In effecting treatment of a patient afflicted with a sleep disorder in accordance with the method of the invention, the non-allosteric $GABA_A$ agonist can be formulated in a manner well-known in the art using common pharmaceutical adjuvants and optionally in combination with other active substances to form common galenic preparations, such as tablets, coated tablets, capsules, powders, suspensions, injectable solutions or suppositories.

In accordance with the method of the invention, the compounds can be administered in any form or mode which makes the compound bioavailable in effective amounts, including oral and parenteral routes. For example, the compounds can be administered orally, subcutaneously, intramuscularly, intravenously, transdermally, intranasally, rectally, topically, and the like. Oral administration is generally preferred. One skilled in the art of preparing formulations can readily select the proper form and mode of administration depending upon the particular characteristics of the compound selected, the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

The dose to be administered depends on the patient's age and weight as well as the degree and nature of sleep disorder. Preferably, the non-allosteric $GABA_A$ agonists used according to this invention are administered in a dose of 5 mg to 50 mg per day. The administration may be intravenous or intramuscular. However, oral administration is preferred.

As used herein, the term "hypnotically effective amount" means an amount sufficient to reduce sleep latency, prolong REMS, prolong nonREMS, prolong total sleep or enhance EEG-delta activity during sleep.

The following examples serve to explain the invention in more detail. These examples are understood to be illustrative only and are not intended to limit the scope of the present invention in any way.

EXAMPLE 1

After intraperitoneal administration of placebo (pyrogen-free saline) or muscimol (0,2 and 0,4 mg/kg), the EEG and EMG as well as the brain temperature of adult rats were continuously recorded.

Muscimol resulted in a dose-dependent increase of non-REMS and REMS and a prolongation of REMS and non-REMS episodes. From the spectral analysis of the EEG within nonREMS, it became evident that muscimol, in particular in higher doses, increases the EEG activity in all frequency bands, most potently, however, at lower frequencies (0.5 to 4 Hz), thought to reflect sleep intensity.

EXAMPLE 2

After intraperitoneal administration of placebo (pyrogen-free saline) or THIP (2 and 4 mg/kg), the EEG and EMG as well as the brain temperature of adult rats were continuously recorded.

THIP dose-dependently increased the total amount of nonREMS and lengthened the duration of the nonREMS and REMS episodes. The higher dose of THIP elevated delta activity within nonREMS, generally believed to reflect an increase in nonREMS intensity.

Corresponding results were also obtained using vigabatrin.

Coated tablets:

| 1 tablet contains: | |
|---|---|
| THIP | 40.00 mg |
| microcristalline cellulose | 100.00 mg |
| lactose | 80.00 mg |
| colloidal silicic acid | 25.00 mg |
| talcum (in the core) | 4.50 mg |
| magnesium stearate | 0.50 mg |
| hydroxypropylmethylcellulose | 12.00 mg |
| ironoxide pigment | 0.10 mg |
| talcum (in the coating) | 0.50 mg |
| weight of one coated tablet | approx. 262.60 mg |

We claim:

1. A method for treating a sleep disorder in a patient in need thereof comprising administering to said patient a hypnotically effective amount of 4,5,6,7-tetrahydroisoxazolo(5.4-C)pyridin-3-ol (THIP).

2. The method according to claim 1, wherein said patient is elderly.

3. The method according to claim 1, wherein said sleep disorder is difficulty in falling asleep.

4. The method according to claim 1, wherein said sleep disorder is frequent nocturnal arousal.

5. The method according to claim 1, wherein the amount of THIP administered is 5 to 50 mg per day.

6. A method for treating a sleep disorder in a patient in need thereof comprising administering to said patient a hypnotically effective amount of tiagabine.

7. The method according to claim 6, wherein said patient is elderly.

8. The method according to claim 6, wherein said sleep disorder is nocturnal arousal difficulty in falling asleep.

9. The method according to claim 6, wherein said sleep disorder is frequent nocturnal arousal.

10. The method according to claim 6, wherein the amount of tiagabine administered is 5 to 50 mg per day.

* * * * *